United States Patent
Rout et al.

(10) Patent No.: US 9,199,956 B2
(45) Date of Patent: Dec. 1, 2015

(54) PROCESS FOR CHEMICAL CONVERSION OF CELLULOSE ISOLATED FROM AROMATIC SPENT BIOMASS TO HYDROXYMETHYL FURFURAL

(71) Applicant: COUNCIL OF SCIENTIFIC & INDUSTRIAL RESEARCH, New Delhi (IN)

(72) Inventors: Prasanta Kumar Rout, Lucknow (IN); Ashween Deepak Nannaware, Lucknow (IN); Ram Rajasekharan, Lucknow (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 14/368,478

(22) PCT Filed: Oct. 3, 2012

(86) PCT No.: PCT/IN2012/000663
§ 371 (c)(1),
(2) Date: Jun. 24, 2014

(87) PCT Pub. No.: WO2013/102911
PCT Pub. Date: Jul. 11, 2013

(65) Prior Publication Data
US 2014/0350271 A1    Nov. 27, 2014

(30) Foreign Application Priority Data
Jan. 3, 2012  (IN) ............................ 0012/DEL/2012

(51) Int. Cl.
C07D 307/46    (2006.01)
C07D 307/48    (2006.01)
C07D 307/50    (2006.01)

(52) U.S. Cl.
CPC ............ *C07D 307/46* (2013.01); *C07D 307/48* (2013.01); *C07D 307/50* (2013.01)

(58) Field of Classification Search
CPC ... C07D 307/46; C07D 307/48; C07D 307/50
See application file for complete search history.

(56) References Cited

FOREIGN PATENT DOCUMENTS

CN    101948452 A    1/2011

OTHER PUBLICATIONS

Sakai, T.,"Highly active and robust organic-inorganic hybrid catalyst for the synthesis of cyclic carbonates from carbon dioxide and epoxides." Green Chemistry 10.3 (2008): 337-341.*
Arumugam, S.K., "One step synthesis of silver nanorods by autoreduction of aqueous silver ions with hydroxyapatite: an inorganic-inorganic hybrid nanocomposite." Journal of Biomedical Materials Research Part A 80.2 (2007): 391-398.*
Wight, A. P.,"Design and preparation of organic-inorganic hybrid catalysts." Chemical reviews 102.10 (2002): 3589-3614.*
Mona, S., "Biosorption of reactive dye by waste biomass of Nostoc linckia." Ecological Engineering 37.10 (2011): 1589-1594.*
Scott, S.A., "Biodiesel from algae: challenges and prospects." Current opinion in biotechnology 21.3 (2010): 277-286.*
Kim, B., "Direct transformation of cellulose into 5-hydroxymethyl-2-furfural using a combination of metal chlorides in imidazolium ionic liquid." Green Chemistry 13.6 (2011): 1503-1506.*
Meixuan Tan et al.: "Production of 5-hydroxymethyl furfural from cellulose in CrCl/Zeolite/BMIMCI system", Biomass and Bioenergy, Pergamon, Amsterdam, NL, vol. 35, No. 3, Dec. 6, 2010.
Database WPI, Week 201131; Thomson Scientific, London, GB: AN 2011-C76274 XP002689801, & CN 101948452A; Jan. 19, 2011.
International Search Report for PCT/IN2012/000663 Dated Jan. 8, 2013.

* cited by examiner

Primary Examiner — Samantha Shterengarts
Assistant Examiner — Matt Mauro
(74) Attorney, Agent, or Firm — Abelman, Frayne & Schwab (57) ABSTRACT

The present invention relates to a process for chemical conversion of cellulose isolated from aromatic spent biomass to hydroxymethyl furfural using an eco-friendly and economical liquids system with recoverable and reusable solid Indion catalysts and zeolite-phosphomolybdic acid hybrid catalysts. The present invention further relates to the preparation of an effective hybrid catalyst i.e. zeolite-phosphomolybdic acid catalyst for synthesis of HMF. The selectivity and yield of HMF is nearly doubled in zeolite-phosphomolybdic acid hybrid catalyst compared to the individual catalysts (zeolite or phosphomolybdic acid) or combination of catalysts viz. zeolite and phosphomolybdic acid.

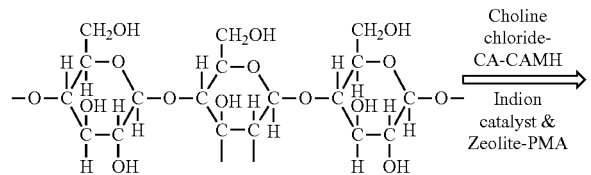

Cellulose

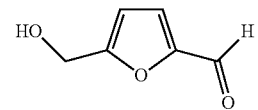

Hydroxymethyl furfural

11 Claims, 2 Drawing Sheets

PROCESS FOR CHEMICAL CONVERSION OF CELLULOSE ISOLATED FROM AROMATIC SPENT BIOMASS TO HYDROXYMETHYL FURFURAL

CROSS-REFERENCE TO RELATED APPLICATIONS

This application is a National Phase of PCT/IN2012/000663, filed Oct. 3, 2012, which claims the priority of Indian Application No. 12/DEL/2012, filed Jan. 3 2012, the disclosures of which are incorporated herein by reference.

FIELD OF THE INVENTION

The present invention relates to the development of green process for preparation of hydroxymethyl furfural (HMF) from cellulose isolated from aromatic spent biomass. The synthesis of HMF from cellulose is completely environment-friendly and economical process. The present invention particularly relates to the preparation of hydroxymethyl furfural (HMF) from cellulose using solid Indion catalysts and zeolite-phosphomolybdic acid hybrid catalysts. The present invention further relates to the preparation of an effective hybrid catalyst i.e. zeolite-phosphomolybdic acid catalyst for synthesis of HMF.

BACKGROUND OF THE INVENTION

A major product in the acid catalysed dehydration of glucose or cellulose is 5-hydroxymethyl-2-furfuraldehyde, also known as hydroxymethyl furfural (HMF). The structure of HMF is shown below:

HMF represents one key intermediate substance for substitute of petrochemicals and is readily accessible from renewable sources like carbohydrates. Energy consumption throughout the world has steadily risen over the last century and is expected to increase at a faster rate due to the rapid development throughout the world. Thus, in order to meet this growing energy demand of the world, lignocellulose biomass has come up as a strong candidate for the production of various valuable petroleum products. Experts throughout the world consider lignocellulose biomass as the only sustainable source of clean energy which can meet the current world growing energy demand. Lignocellulosic biomass has the potential to displace the petroleum derived product, which is presently used as transportation fuels. Now-a-days, the researchers have only used model biomass compounds (fructose, glucose, inulin, etc), that do not contain the impurities present in biomass feed stocks for preparation of chemicals. A suitable green technology for the production of various useful bio-chemicals directly from biomass has not been developed so far.

India produced more than 6.0 million tons per annum of aromatic spent biomass. Some of the major aromatic crops cultivated in India includes mentha, citronella, lemongrass, pamarosa, patchouli, etc. These aromatic crops contain 4-8 w/w % of essential oil. After extraction of the valuable essential oil by steam or hydrodistillation method, the spent biomass is of no use and treated as waste material. People generally used this spent distilled biomass for burning purpose which also leads to environment related problems. This patent describes the development of sustainable, integrated and holistic strategies for the production of various valuable biochemical. The major constituent present in aromatic spent biomass is cellulose (35-40%), hemicellulose (25-30%) and lignin (15-20%). Cellulose is a major biopolymer of glucose unit, is used for synthesis of HMF. It is known that, the high boiling point of HMF (291° C.) is the limitation factor to be used as fuel. But, HMF can be used for the production of 2,5-dimethyl furan (DMF) which has a high calorific value. Also, DMF has the lowest water solubility and the highest research octane number or RON (106) among mono-oxygenated C6 compounds. Its physicochemical properties are competitive to ethanol. Its energy density (31.5 MJ/l) is 40% higher than ethanol (23 MJ/l) and much closer to gasoline (35 MJ/l). DMF has better anti-knock quality than gasoline. It has higher boiling point (92° C.) than ethanol (78° C.), which made it less volatile and an ideal factor for liquid transportation fuel. HMF can be used for the production of various valuable bio-chemicals like chiral reagents, biologically active materials, polyhydroxyalkanoates, polymers and polymerization initiators, antifouling compounds, personal care products, lubricants, adsorbents, printing inks, coatings, electronics, photography, batteries, drug delivery, corrosion inhibitors, bio-pesticides, etc.

Aromatic spent biomasses represent one of the most abundant and underutilized biological resources on the planet. From the olden times, these biomasses were simply used to burn and generate thermal energy. Nowadays, utilization of these lignocellulosic biomasses can produce liquid bio-fuels and value added chemicals.

Many researchers around the world have tried and produced HMF from various sources of carbohydrates like glucose, fructose, inulin, sucrose etc. These food grade carbohydrates (sugars) are easily soluble in water. It is straightforward to convert these carbohydrate solutions directly into HMF. Some researchers have reported the use of high boiling point solvents such as butanol, methyl isobutyl ketone, dimethyl acetamide, dimethyl formamide, DMSO etc to produce HMF from sugar solution. Some researchers have also mentioned the process of treating the sugar solution with metal chlorides such as $CrCl_2$, $CrCl_3$, $CuCl_2$, $FeCl_2$, $RuCl_2$ etc or Amberlyst resins or Dowex resins or mineral acids as catalyst at high temperature (120 to 150° C.) for synthesis of HMF. But very limited researchers around the world are able to produce HMF from lignocellulosic waste biomass.

Carbohydrates like fructose are very easily converted into HMF. Fructose easily gets dissolved in various organic and aqueous solvents and follows a single step (dehydration) for conversion to HMF. A study lead by Ilgen et al., (Green Chem. 2009, 11, 1948) reported the conversion of fructose to HMF. In their study, they have used choline chloride-citric acid (ChCl-CA) solution for carrying out the reaction. Fructose being the simplest monosaccharide, it gets converted to HMF even in the absence of catalyst in high-boiling solvents such as DMSO, DMF and DMA. It is reported that some food grade carbohydrates (fructose, glucose, sucrose, etc) also contained HMF as degraded chemical in heat processing of these reducing carbohydrates, which indirectly determines the inferior quality of food product. Very limited researchers around the world are able to produce HMF from lignocellulosic waste biomass. In our patented process, we have developed a novel eutectic solvent medium for cellulose dissolution and a novel hybrid catalyst for carrying out the reaction.

Many researchers have tried to use expensive imidazolium chloride based ionic liquids (ILs) for cellulose dissolution and HMF production. D Argyropoulos in his patented study (WO/2008/098036) reported the use of acid catalyst and expensive imidazolium chloride based ILs for carrying out the thermolysis process of lignocellulosic biomass. But this process is not commercially viable due to the expensive nature of ILs. Another study lead by Jong et al. group (WO2011149341) reported the production of HMF from lignocellulosic biomass using a combination of expensive ILs and organic acid. This process is also not commercially viable due to the expensive nature of ILs and recoverable limitation of organic acid as catalyst. Su et. al. (Applied Catalysis A; 361, 2009, 117) also reported the use of expensive imidazolium chloride based ILs for cellulose dissolution. In their study, they reported the use of ILs for dissolving the pure cellulose and higher yield of HMF. Though this process offered appreciable yield of HMF, but it cannot be practiced in the industrial scale due to expensive ILs. Another study lead by Dhepe et al., (WO/2011/092711) group describes single step hydrolytic process for converting lignocellulose mainly xylan (xylose) into furfural. In their study, they have used common organic solvent (alcohol, ether, ester, hexane, acids, toluene, xylene) to dissolve the hemicellulose (xylan) and expensive dowex resin as catalyst for carrying out the reaction. In this process, they mainly targeted the easily soluble hemicellulose for the furfural production and failed to explain the dissolution of cellulose in a solvent system and the production of HMF. In their process, they have claimed, 40% yield of furfural production from xylose, obtained from hemicellulose.

Some of the researchers have also used different combination of solvents dimethyl acetamide-LiCl and expensive imidazolium chloride based ionic liquid for conversion to HMF. Study leads by Binder and Raines (J. Am. Chem. Soc. 131, 2009, 1979) reported the use of dimethyl acetamide-LiCl solvent system for cellulose dissolution and HMF production. In this process, they have used low cost solvents but the main constraint arises in this system is the isolation of HMF from the reaction mixture. It has been reported that, the physical and chemical properties of both the dimethyl acetamide and HMF are very close together (having very close boiling point). Hence, it is very difficult to separate the product HMF from the reaction solution i.e dimethyl acetamide. Similarly, LiCl is also soluble in most of the extracting solvents and again needs extensive isolation process for getting the reasonable pure HMF. This separation problem of HMF added cost to this process. Apart from isolation difficulties, using this solvent the reasonable yield of HMF is possible only with an addition of imidazolium chloride ILs in DMA-LiCl system. The use of ILs along with DMA-LiCl, make this process expensive. All this processes discussed above are expensive and having separation limitation.

Background of the Preparation of 5-Hydroxymethyl Furfural

HMF and 2,5-disubstituted furanic derivatives have great potential in the field of intermediate chemicals from the re-growing resources. Due to their various functionalities, HMF could be utilized for producing wide range of products. Most of the works throughout the world have reported on the synthesis of HMF from fructose. HMF represents one key intermediate substance and can be used as a suitable starting source for the manufacture of various furan monomers. The reaction mechanism for synthesis of HMF follows cyclic fructofuranosyl intermediate pathways. Regardless, the mechanism of HMF formation, the intermediate species formed during the reaction may in turn undergo further reactions such as condensation, rehydration, reversion and other rearrangements, resulting in a plethora of unwanted side products.

Although preparation of HMF has been known for many years, a method which provides HMF with good selectivity and in high yields has yet to be discovered. The complications arose from the rehydration of HMF, which yielded the by-products such as levulinic acid and formic acid. Another unwanted side reaction included the polymerization of HMF and/or fructose resulting in humin polymers, which were solid waste products. Further complications could arise as a result of solvent selection. Water is easy to dispose of and dissolves fructose, but unfortunately low selectivity and increased formation of polymers and humin increased under aqueous conditions.

Agricultural raw materials such as cellulose, sucrose or inulin are inexpensive starting materials for the manufacture of hexoses (glucose and fructose). As discussed above, these hexoses could be converted to HMF. The dehydration of sugars to produce HMF is well known. HMF was initially prepared in 1895 from levulose by Dull (Chem. Ztg., 19, 216) and from sucrose by Kiermayer (Chem. Ztg., 19, 1003). However, these initial syntheses were not practical methods for commercial scale production of HMF due to very low conversion of the starting material. Commonly used catalysts for the preparation of HMF includes corrosive inorganic acids such as $H_2SO_4$, $H_3PO_4$, and HCl, etc. These acid catalysts were used in solution and are very difficult to regenerate and dispose. In order to avoid this regeneration and disposal problems, solid catalysts have been used in the present process.

The purification of HMF has also proved to be a troublesome operation. On long exposure to high temperatures at which the desired product can be distilled, HMF and impurities associated with the synthetic mixture tend to form the degradation products. Because of this heat instability, a falling film vacuum still must be used. Even in such an apparatus, resinous solids form on the heating surface causing a stalling in the rotor and frequent shut down time making the operation inefficient. Prior work has been performed with distillation and the addition of a non-volatile solvent like PEG-600 to prevent the buildup of solid humin polymers. On the other hand, the use of polyglycols leads to the formation of HMF-PEG ethers. The prior art processes also fail to provide a method for producing HMF that can be performed economically.

Although preparation of HMF has been known since 1895, but a method which provides HMF with eco-friendly route, good selectivity and high yields has not been developed so far.

Following are some of the most important processes known related to the production of HMF:

(a) Most of the processes claim the synthesis of the HMF from glucose or fructose or inulin or sucrose using high boiling point solvents such as butanol, methyl isobutyl ketone, dimethyl acetamide, dimethyl formamide, DMSO etc. The sugar solution was treated with metal chlorides such as $CrCl_2$, $CrCl_3$, $CuCl_2$, $FeCl_2$, $RuCl_2$ etc or Amberlyst resins or Dowex resins or mineral acids as catalyst at high temperature (120 to 150° C.) for synthesis of HMF. The dehydration of fructose is quite facile; even in the absence of catalyst in high-boiling solvents such as DMSO, DMF and DMA, whereas glucose requires a special catalyst for the formation of HMF. Therefore, the synthesis of HMF from food derived products is a very easy process.

On the other hand, conversion of fructose to HMF in choline chloride-citric acid (ChCl-CA) has been reported (Ilgen et al., Green Chem., 11, 1948). But no work on synthesis of HMF from cellulose (Complicated plant based biopolymer) using this combination has been reported. Structurally, fructose and cellulose are entirely different molecule. Cellulose having a stable regular long chain polysaccharides of glucose molecules link by β-1,4 glycoside linkage. Hence it is very difficult to dissolve and break this β-1,4 glycoside linkage of cellulose molecule. Whereas fructose is a simple monosaccharide, which is easily dissolve in various organic or aqueous solvents and follows only one step process for conversion to HMF.

(b) Some of the processes claim the use of imidazolium based ionic liquids such as 1-ethyl-3-methyl imidazolium chloride, 1-butyl-3-methyl imidazolium chloride, 1-ethyl-3-methyl imidazolium acetate, 1-ethyl-3-methyl imidazolium hydrogen chloride, 1-butyl-3-methyl imidazolium acetate, 1-butyl-3-methyl imidazolium hydrogen chloride, 1-ethyl-3-methyl imidazolium hydrogen sulphate and 1-butyl-3-methyl imidazolium hydrogen sulphate, etc. for dissolving the microcrystalline cellulose. Then, the cellulose solution is treated with metal chlorides such as $CrCl_2$, $CrCl_3$, $CuCl_2$, $FeCl_2$, $RuCl_2$, etc or mineral acids or zeolite or Amberlyst, Dowex resins as catalyst at high temperature (120 to 150° C.) for synthesis of HMF. Su et al. (Appl. Catal. 2009, 361, 117) have prepared the HMF by using combination $CrCl_2$ and $CuCl_2$ catalysts. But, they used the expensive ionic liquid (1-ethyl-3-methyl imidazolium chloride) as the reaction medium for dissolution of cellulose.

(c) Limited reports are available on the use of mixture of dimethyl acetamide-LiCl (DMA-LiCl) for dissolving the cellulose. Mechanistic analyses reveal that loosely ion-paired halide ions in DMA-LiCl are critical for weakening the cellulosic β-1,4-glycosidic linkages. Though, DMA-LiCl is able to solubilise the cellulose but conversion of cellulose to HMF is poor in this solvent system. Binder and Raines (J. Am. Chem. Soc. 2009, 131. 1979) have reported the synthesis of HMF by using DMA-LiCl solvent system along with 1-ethyl-3-methyl imidazolium chloride using metal chlorides such as $CrCl_2$, $CrCl_3$, etc or mineral acids as catalyst.

In the hitherto known processes, especially the first category (a) is feasible because the sugar solutions (monosaccharides or disaccharides) are easily soluble in aqueous or polar organic solvents. The HMF is also synthesized from these reduced sugars in mild conditions with high conversion ratio. Second category (b) process needs very expensive imidazolium based ionic liquids for dissolving the cellulose. Though it provides appreciable yield of HMF, but the process cannot be practiced in the industrial scale due to expensive ionic liquid. In the third category (c) process, the cellulose is dissolved by using cheap solvent (DMA-LiCl) system, but it has the separation limitation of reaction product (HMF) from the solvent system. The appreciable yield is only obtained, when DMA-LiCl along with the imidazolium ionic liquid is used as the reaction medium, but major constraint of the process is isolation of HMF from the reaction medium. It is known that the physical and chemical properties of both dimethyl acetamide and HMF are very close together. Also, both solvents boiling point are very high, so it is very difficult and also quite expensive to separate the product (HMF) from the reaction solution (dimethyl acetamide). Similarly, LiCl is also soluble in most of the extracting solvents and again needs extensive isolation process for getting the reasonably pure HMF. Finally, the third category process is not completely free from ionic liquid solvent. From the above literature survey, it is clear that imidazolium based ionic liquids or DMA-LiCl system can solubilise the cellulose, but former one is costly process and later one is reasonably costly along with separation (HMF) limitations.

The catalyst system reported for synthesis of HMF are metal chlorides such as $CrCl_2$, $CrCl_3$, $CuCl_2$, $FeCl_2$, $RuCl_2$, $AlCl_3$ etc or mineral acids or zeolite or Amberlyst, Dowex resins.

Object of the Present Invention

The main object of the present invention is to provide a process for the chemical conversion of cellulose isolated from aromatic spent biomass to hydroxymethyl furfural using an eco-friendly and economical liquid system with recoverable and reusable solid Indion catalysts and zeolite-phosphomolybdic acid hybrid catalysts.

Another object of the present invention is to prepare cellulose solution by using novel choline chloride-citric acid-citric acid monohydrate (ChCl-CA-CAMH) eutectic solvent system which is an inexpensive and an environment friendly solvent system.

Another object of the present invention is to prepare an effective hybrid catalyst i.e. zeolite-phosphomolybdic acid catalyst for isomerisation of glucose to fructose and further synthesis of HMF.

Still another object of the present invention is to develop an economical method for isolation of cellulose from spent aromatic biomass.

SUMMARY OF THE INVENTION

Accordingly the present invention provides a green process for the production of 5-Hydroxymethyl furfural (HMF) comprising following steps:
(a) dissolving cellulose in a choline chloride-citric acid-citric acid monohydrate system;
(b) adding a solid acidic catalyst to the solution as obtained in step (a) and carrying out reaction for a period ranging between 5 to 25 minutes followed by adding a hybrid catalyst and carrying out reaction for a period ranging between 90 to 120 minutes to obtain a reaction mixture;
(c) extracting the reaction mixture as obtained in step (b) with liquid solvent selected from the group consisting of ethyl acetate and methyl isobutyl ketone to obtain a liquid solvent extract and a residual reaction mixture;
(d) reacting the residual reaction mixture as obtained in step (c) with the solid acidic catalyst followed by treating with the hybrid catalyst and extracting as given in step (b) and (c) to obtain a liquid solvent extract and a residual reaction mixture;
(e) combining the liquid solvent extracts obtained in step (c) and step (d) and concentrating to obtain 5-Hydroxymethyl furfural (HMF), followed by purification of HMF by column chromatography;

In an embodiment of the invention, steps (a) and (b) are carried out at a temperature in the range of 120° C. to 140° C.

In another embodiment of the invention, the cellulose used in step (a) is prepared by a process comprising the following steps:
(i) pulverizing dried spent biomass to size less than 0.1 mm;
(ii) treating pulverized spent biomass with a mixture of equal amounts of solvent (hexane:ethyl acetate:alcohol) to isolate lipids and waxes for obtaining defatted biomass;

(iii) treating the defatted biomass as obtained in step (ii) with aqueous $NaClO_2$ solution followed by aqueous NaOH solution, to obtain a residue;

(iv) treating the residue obtained in step (iii) with combination of pre-cooled aqueous NaOH, urea and thiourea solution to obtain processed cellulose.

In another embodiment of the invention, the choline chloride-citric acid-citric acid monohydrate system used in step (a) is prepared by mixing choline chloride, citric acid and citric acid monohydrate in the ratio of 4:1:1 (by weight) at 85 to 95° C.

In another embodiment of the invention, the solid acidic catalyst used in step (b) is selected from the group consisting of Indion 225H and Indion 790.

In another embodiment of the invention, the hybrid catalyst used in step (b) is selected from the group consisting of γ-H-zeolite-phosphomolybdic acid and β-H-zeolite-phosphomolybdic acid.

In another embodiment of the invention, hybrid catalyst selected from the group consisting of γ-H-zeolite-phosphomolybdic acid and β-H-zeolite-phosphomolybdic acid is synthesized by a process comprising the following steps:

[i] mixing 55-65% of phosphomolybdic acid and 35-45% of zeolite selected from the group consisting of γ-H-zeolite and β-H-zeolite, in aqueous medium followed by stirring the mixture for a period ranging between 1 to 2 h to obtain a reaction mixture;

[ii] drying the reaction mixture as obtained in step (i) followed by calcinating at a temperature ranging between 500 to 550° C. to obtain the hybrid catalyst.

In another embodiment of the invention, calcination of reaction mixture to obtain the hybrid catalyst is done for a period ranging between 7 to 8 h.

In another embodiment of the invention, the solid acidic catalyst, the hybrid catalyst and the choline chloride-citric acid-citric acid monohydrate system from the reaction mixture obtained in step (d) is recycled for use.

In another embodiment of the invention, the solid acidic catalyst and the hybrid catalyst is recycled by a process comprising the following steps:

i. diluting the residual reaction mixture as obtained in step (d) of claim 1 with alcoholic solvent selected from the group consisting of methanol and ethanol to obtain a precipitate of un-reacted cellulose and a mixture of catalysts;

ii. washing the precipitate with water to remove the unwanted carbon particles followed by separating the un-reacted cellulose and mixture of catalysts by gravity separation technique;

iii. separating the solid acidic catalyst and the hybrid catalyst from the mixture of catalysts by gravity separation technique, followed by washing with water and ethanol and drying;

iv. calcinating the hybrid catalyst at a temperature ranging between 500 to 550° C.

In another embodiment of the invention, the choline chloride-citric acid-citric acid monohydrate system is recycled in step (f) by a process comprising the following steps:

i. diluting the residual reaction mixture as obtained in step (d) of claim 1 with alcoholic solvent selected from the group consisting of methanol and ethanol to dissolve the choline chloride-citric acid-citric acid monohydrate;

ii. filtering the solution to obtain a filtrate and charcoaling the filtrate for removing dark red colour from the filtrate;

iii. concentrating the charcoaled filtrate under vacuum to obtain the choline chloride-citric acid-citric acid monohydrate system.

In another embodiment of the invention, concentration of the liquid solvent extract in step (e) is done by distillation to obtain the 5-Hydroxymethyl furfural.

In another embodiment of the invention, the 5-Hydroxymethyl furfural is purified by column chromatography using 60 to 200 mesh size silica gel and 35 to 45% acetonitrile in dichloromethane.

DETAILED DESCRIPTION OF THE DRAWINGS

DETAILED DESCRIPTION OF THE INVENTION

The aromatic biomasses such as mentha, citronella, lemongrass, pamarosa, patchouli, etc are collected after extraction of the essential oil. These biomasses are then sun-dried and pulverized with the help of ball mill (~1 mm size). The isolation of cellulose from aromatic spent biomass is very difficult due to the complex hierarchical linkages between cellulose, hemicellulose and lignin. Further, the waxes present on the surface of the biomasses inhibit the percolation of acid/alkali solution into the biomass.

The pulverized biomass is first extracted in a Soxhlet apparatus or stirred reactor at 65° C. for about 5 h with solvent system comprising of equal volumes of hexane, ethyl acetate and ethanol. The soxhlet or stirred reactor extraction facilitates the removal of waxy components and chlorophyll from the biomass. The de-waxed biomass is then dried and kept at room temperature for the isolation of lignin, cellulose and hemicellulose. The de-waxed biomass is then treated with 1% $NaClO_2$ solution at 65 to 80° C., to remove the lignin. The delignified biomass is treated with 6% NaOH solution and the reaction mixture is stirred at 65 to 80° C. for 15 minutes and then the mixture is filtered. The filtrate is maintained at a pH in between 5.0 to 5.5, about 3 volumes of methanol/ethanol is added in that solution to precipitate the hemicellulose. The hemicellulose is recovered from the solution by filtration. The residue (NaOH treated) is again treated with a combination of pre-cooled (5° C.) 7 to 8% NaOH, 7 to 8% urea and 5 to 6% thiourea solution for 15 minutes. The solution is filtered and the residue obtained is washed with distilled water. The residue (cellulose) is then dried and kept at room temperature for further reaction to HMF.

Aromatic spent biomasses used in this process have been taken from the CSIR-CIMAP farm. Being a Medicinal and Aromatic Plants Research Institute, various types of aromatic plants are being cultivated in CSIR-CIMAP. Aromatic plants, which were used in research include: Mentha, Palmarosa, Lemongrass, Patchouli, Citronella, Etc. Geographically all these aromatic plants are cultivated and located in Lucknow.

Figure 1:
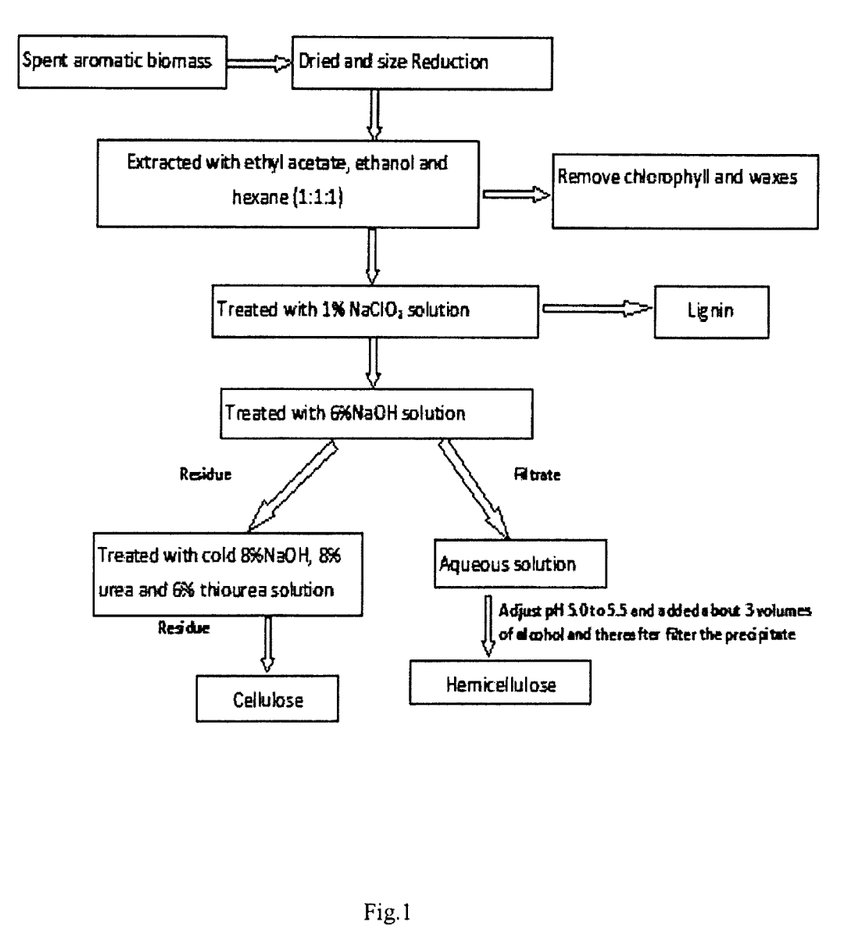
FIG. 1 is a flow chart of each step of the isolation of cellulose from spent aromatic biomass.

The flow chart for better understanding of each step for the isolation of cellulose from spent aromatic biomass is given in FIG. 1.

Preparation of Catalyst

Zeolite is silica-alumina based catalyst and phosphomolybdic acid is heteropoly acid based catalyst. The new hybrid catalyst viz. zeolite-phosphomolybdic acid is prepared by the following procedure. Phosphomolybdic acid (3 g) is added in 7 mL water to prepare the paste. Then after, in this paste, 2 g of γ-H-zeolite or β-H-zeolite is added and stirred the reaction mixture for about 2 h. Then, the catalyst paste is dried in oven at 105° C. for 2 h. Finally, catalysts are calcinated at 500 to 550° C. for 7 to 8 h to obtain γ-H-zeolite-phosphomolybdic acid or β-H-zeolite-phosphomolybdic acid hybrid catalysts.

The Indion catalysts are economical, selective and provide improved yield of HMF. Similarly, the catalytic property of zeolite-phosphomolybdic acid hybrid catalyst is far better in comparison to the individual zeolite and phosphomolybdic acid or using equivalent ratio of both. The new hybrid catalyst has shown better selectivity with improved yield of the HMF. The combination of both catalysts is showing better selective and yield of HMF in Choline chloride-citric acid-citric acid monohydrate (ChCl-CA-CAMH) system. These catalysts after recovering from the reaction medium, shows similar efficiency in number of use for subsequent batches. These hybrid catalysts (γ-H-zeolite-phosphomolybdic acid or β-H-zeolite-phosphomolybdic acid) are thermally stable and not reported so far.

Reaction Mechanism

The reaction mechanism for synthesis of HMF follows cyclic fructofuranosyl intermediate pathways. Initially, cellulose is de-polymerised to glucose in the presence of acidic (Indion) catalyst. Thereafter, glucose isomerizes to fructose in the presence of acidic zeolite-PMA based catalyst. In the course of reaction, three molecules of water are lost in the presence of catalyst, and finally fructose is converted to hydroxymethyl furfural (HMF). The schematic reaction mechanism for synthesis of HMF from cellulose is as given below:

Thereafter, γ-H-zeolite-phosphomolybdic acid or β-H-zeolite-phosphomolybdic acid hybrid catalyst is added to the reaction solution and stirred another 90 to 120 minutes. Finally, the reaction mixture is extracted by ethyl acetate/methyl isobutyl ketone (MIBK). The same residual reaction mixture is continued for second time with additional amounts of Indion and zeolite-phosphomolybdic acid hybrid catalyst for 90 to 120 minutes. Again, the reaction mixture is extracted by ethyl acetate/MIBK. In the end of two batch process, both the ethyl acetate/MIBK extract are combined and the ethyl acetate/MIBK are removed in rotary evaporator under vacuo to get the HMF. The yield of HMF in the present process is 35 to 40%.

After removing the HMF from the reaction mixture, the residue is treated with methanol or ethanol, to precipitate the un-reacted cellulose, Indion and zeolite-PMA catalysts. Then the solution is filtered, charcoaled and concentrated under vacuo to obtain the re-generated solvent system (ChCl-CA-CAMH). This reaction mixture is used for another fresh batch reaction. On the other hand, the residue is thoroughly washed with distilled water to remove the carbon particles. The catalysts are recovered from the aqueous reaction mixture by gravity separation. The un-reacted cellulose is isolated by filtration. The filtrate is again centrifuged to obtain the additional amounts of catalysts. The un-reacted cellulose, Indion and zeolite-PMA catalysts are re-used for another batch reaction. The catalysts and reaction mixture are used at least five times with similar efficiency.

Advantage of the Reaction Medium

Choline chloride-citric acid-citric acid monohydrate (ChCl-CA-CAMH) solution dissolves the cellulose similar to an ionic liquid. Viscosity of cellulose in ChCl-CA-CAMH system is found to be similar with the cellulose solution in ionic liquid system and, the extraction and yield of final product (HMF) in both the system is almost within the range. Our new solution i.e. the ChCl-CA-CAMH system can be recovered and re-used for number of times with almost similar efficiency. This ChCl-CA-CAMH system is not reported so far for dissolving the cellulose.

Procedure of the Experiment

The clear solution of choline chloride-citric acid-citric acid monohydrate (ChCl-CA-CAMH) (4:1:1) is prepared at 85 to 95° C. The cellulose is added into this solution system in the ratio of 1:20 (cellulose: ChCl-CA-CAMH). The reaction mixture is stirred at 120 to 140° C. for 3 to 4 h, to obtain reddish or brownish color solution. Then cooled the reaction mixture, Indion 225H or Indion 790 is added and the reaction mixture is stirred for 5 to 25 minutes at 120 to 140° C.

Figure 2:
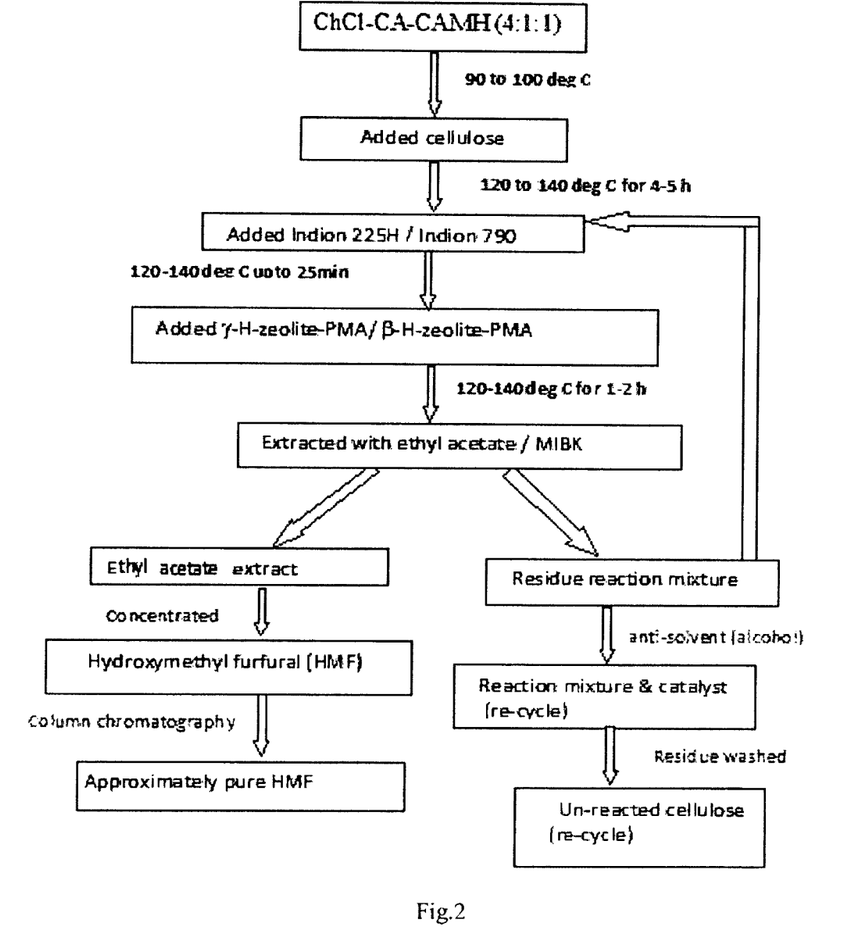
FIG. 2 is a flow chart of each step in the synthesis of HMF from isolated cellusose.

The flow chart for better understanding of the each step for the synthesis of HMF from isolated cellulose is given in FIG. 2.

The present invention provides a newer process for the production of hydroxymethyl furfural (HMF) from cellulose. The synthesis of HMF from cellulose is the main concern due to its limited solubility in aqueous or organic solvents. As already discussed, cellulose is well dissolved in imidazolium based ionic liquid, but it is very expensive solvent. Similarly, the solvent system like dimethyl acetamide-LiCl can also solubilise the cellulose, but the main constraint arising in this system is isolation of HMF from the reaction mixture and a reasonable yield of HMF is possible with adding imidazolium chloride ILs in DMA-LiCl system. In our present study, we have dissolved the cellulose in a cheap and biodegradable solvent system (choline chloride-citric acid-citric acid monohydrate). The solubility of cellulose in choline chloride-citric acid-citric acid monohydrate (ChCl-CA-CAMH) solvent system has not been reported so far. In our study, we have developed a newer process for the synthesis of HMF from cellulose using cheap combined catalysts viz. Indion 225H or Indion 790 and γ-H-zeolite-phosphomolybdic acid or β-H-zeolite-phosphomolybdic acid. These catalysts are added into the cellulose solution in two steps which improve the yield of HMF.

Following are the steps involved in the complete process:

(i) The dried aromatic spent biomass (mentha, citronella, lemongrass, pamarosa, patchouli) was collected and pulverized to small size (<0.1 mm).
(ii) These dried grinded aromatic spent biomasses are used for the isolation of cellulose.
(iii) The grinded biomass is treated with equal amounts of solvent (hexane:ethyl acetate:alcohol) in a single step for isolation of lipids and waxes.
(iv) The defatted biomass is treated with aqueous $NaClO_2$ solution for removing the lignin.
(v) The delignified biomass is treated with aqueous NaOH solution in first step and residue is again treated with a combination of pre-cooled (~5° C.) aqueous NaOH, urea and thoiurea solution. The final residue obtained is cellulose. The hemicellulose is obtained from first aqueous NaOH solution by alcoholic precipitation at pH less than 5.5.
(vi) The urea and thiourea treated biomass/cellulose is less crystalline (more amorphous character) as compared to the original cellulose.
(vii) The isolated cellulose is then dissolved in ChCl-CA-CAMH mixture to obtain the slightly reddish or brownish solution.
(viii) The preparation of new hybrid catalysts viz. γ-H-zeolite-phosphomolybdic acid or β-H-zeolite-phosphomolybdic acid for better catalytic activity.
(ix) First the cellulose solution is treated with Indion 225H or Indion 790 (solid acid catalysts) for depolymerisation of cellulose, followed by γ-H-zeolite-phosphomolybdic acid or β-H-zeolite-phosphomolybdic acid hybrid catalyst for the synthesis of HMF. After addition of catalyst, the reaction is carried out for about 2 h at 120 to 140° C.
(x) After the reaction, HMF is then extracted from reaction mixture by liquid-solvent extraction system using ethyl acetate/methyl isobutyl ketone as extracting solvent.
(xi) The residual reaction mixture obtained is then again reacted with solid acidic catalyst followed by hybrid catalyst and carrying out reaction for another 2 h (appox.) at same temperature to get the additional amounts of HMF. Similarly, the HMF is isolated from reaction mixture by liquid-solvent extraction (ethyl acetate/methyl isobutyl ketone).
(xii) Both the extracts obtained from steps (x) and (xi) (ethyl acetate/methyl isobutyl ketone) are combined and the solvent is removed by distillation to obtain the HMF. The yield of HMF obtained is about 35 to 40% (on the basis of the cellulose taken for the reaction).
(xiii) The HMF extract is further purified in column chromatography by using 35 to 45% acetonitrile in dichloromethane.
(xiv) After the reaction, the residual reaction mixture is then dissolving in methanol/ethanol/acetone to separate the solid Indion catalysts, zeolite-PMA and un-reacted cellulose. The alcoholic/acetone solution is filtered and concentrated after charcoaling to re-generate the liquid system, which is used for another fresh batch reaction.
(xv) The percentage of un-reacted cellulose obtained is around 30 to 35%. The crystalline structure of this obtained cellulose is disrupted and they are easily soluble in the liquid system (ChCl-CA-CAMH). This un-reacted cellulose is further re-used for another batch of reaction.
(xvi) The recovered solid acidic catalyst (Indion 225H or Indion 790) is thoroughly washed with water and ethanol. It is then dried to regenerate the catalytic activity. The same catalyst is again used for another batch of reaction. Similarly, zeolite-phosphomolybdic acid is recovered and re-used in another batch of reaction.

EXAMPLES

Following Examples are Given by Way of Illustration of the Invention and should not be Construed to Limit the Scope of the Present Invention Example 1

Air dried and pulverized spent mentha biomass (100 g) was extracted with mixture of hexane (about 150 mL), ethyl acetate (about 150 mL) and ethanol (about 150 mL) in Soxhlet apparatus for about 5 h. The mixture of solvents was concentrated under vacuum and weight of the extract was 7.3 g (7.3%). This extract contains chlorophyll, lipids and hydrocarbons along with trace amounts of other components. After drying, the weight of the biomass was 87 g (approx). The extracted biomass (10 g) was treated with 1% $NaClO_2$ solution and kept at 80° C. for 30 minutes. Then the solution was filtered and concentrated and the lignin content was 1.5 g. The delignified biomass (residue) was treated with 6% of NaOH solution (about 30 mL) for about 15 minutes at 80° C. and filtered. The pH of the filtrate was adjusted to 5.5 and then, about 80 mL of ethanol was added in the solution to precipitate the hemicellulose. The hemicellulose was isolated from the solution by filtration and washed in distilled water. The weight of the hemicellulose was 2.5 g. Again the residue was treated with pre-cooled (5° C.) 8% NaOH solution (about 10 mL), pre-cooled (5° C.) 8% urea solution (about 10 mL) and pre-cooled (5° C.) 6% thiourea solution (about 10 mL), for about 15 minutes. Then, the solution was filtered and residue was washed with distilled water to get the cellulose 3.5 g.

The homogeneous solution of choline chloride (ChCl, about 13.3 g), citric acid (CA, 3.3 g) and citric acid monohydrate (CAMH, about 3.3 g) was formed at 90° C. In this solution (ChCl-CA-CAMH), 1 g of cellulose isolated from mentha spent biomass was added and the reaction mixture was stirred at 140° C. for 4 h to obtain reddish or brownish coloured solution. Thereafter, 200 mg of Indion 225H was added and the whole reaction mixture was stirred for 20 minutes at 130° C. Thereafter, the reaction mixture was cooled to room temperature and hybrid catalyst of γ-H-zeolite-phosphomolybdic acid (50 mg) was added and stirring continued for another 2 h at 130° C. Then, the reaction mixture was extracted with ethyl acetate (about 20 mL). Again the residual reaction mixtures were treated with Indion 225H (about 100 mg) and γ-H-zeolite-phosphomolybdic acid (15 mg) and continue stirring at 130° C. for 2 h. Then, the reaction mixture was extracted with ethyl acetate (about 20 mL). Both the ethyl acetate extracts were combined and concentrated in rotary evaporator under vacuum to obtained HMF (about 300 mg, 40%). The HMF was further purified by column chromatography using silica gel (60 to 120 mesh). The column was eluted with 35% acetonitrile in dichloromethane to obtain the approximate purified HMF (about 250 mg, 35%)

Example 2

Air dried and pulverized spent biomass of palmarosa (100 g) was extracted with mixture of hexane (about 150 mL), ethyl acetate (about 150 mL) and methanol (about 150 mL) in Soxhlet apparatus for about 5 h. The mixture of solvents was concentrated under vacuum and weight of the extract is 7.5 g (7.5%). The extract contains chlorophyll, lipids and hydrocarbons along with trace amounts of other components. After drying, the weight of the biomass was 86 g (approx). The extracted biomass (10 g) is treated with 1% $NaClO_2$ solution and kept at 80° C. for 30 minutes. Then filtered the solution and concentrated, the lignin content is 1.6 g. The delignified biomass (residue) was treated with 6% of NaOH solution (about 30 mL) for about 15 minutes at 65° C. and filtered. The pH filtrate was adjusted to 5.2 and then, about 80 mL of ethanol was added in the solution to precipitate the hemicellulose. The hemicellulose was isolated from the solution by filtration and washed in distilled water. The weight of the hemicellulose is 2.4 g. Again the residue was treated with pre-cooled (5° C.) 7% NaOH solution (about 10 mL), pre-cooled (5° C.) 7.5% urea solution (about 10 mL) and pre-cooled (5° C.) 5.5% thiourea solution, for about 15 minutes. Then, filter the solution and residue was washed with distilled water and acetone to get the cellulose 3.7 g.

The homogeneous solution of choline chloride (ChCl, about 13.3 g), citric acid (CA, 3.3 g) and citric acid monohydrate (CAMH, about 3.3 g) was formed at 85° C. In this solution (ChCl-CA-CAMH), 1 g of isolated cellulose from palmarosa spent biomass was added and stirred the reaction mixture at 135° C. for 4 h to obtain reddish or brownish coloured solution. Thereafter, Indion 790 (200 mg) was added and the whole reaction mixture stirred for 5 minutes at 130° C. Then the reaction mixture was cooled to room temperature, and 0.5 mL of distilled water was added to it, followed by stirring at 130° C. for 15 minutes. Thereafter, the reaction mixture was cooled to room temperature and hybrid catalyst of γ-H-zeolite-phosphomolybdic acid (50 mg) was added and stirring continued for another 2 h at 130° C. Then, the reaction mixture was extracted with methyl isobutyl ketone (MIBK) (about 20 mL). Again the residual reaction mixture was treated with Indion 790 (about 100 mg) and γ-H-zeolite-phosphomolybdic acid (15 mg) and stirring continued at 130° C. for 2 h. Then, the reaction mixture was extracted with MIBK (about 20 mL). Both the MIBK extracts were combined and concentrated in rotary evaporator under vacuum to obtain the HMF (about 300 mg, 40%). The HMF was further purified by column chromatography using silica gel (60 to 120 mesh). The column was eluted with 40% acetonitrile in dichloromethane to obtain the approximate purified HMF (about 250 mg, 35%).

Example 3

Air dried and pulverized spent biomass of lemongrass (100 g) was extracted with mixture of hexane (about 150 mL), ethyl acetate (about 150 mL) and ethanol (about 150 mL) in Soxhlet apparatus for about 5 h. The mixture of solvents was concentrated under vacuum and weight of the extract was 7.5 g (7.5%). The extract contains chlorophyll, lipids and hydrocarbons along with trace amounts of other components. After drying, the weight of the biomass was 88 g (approx). The extracted biomass (10 g) was treated with 1.2% $NaClO_2$ solution and kept at 70° C. for 30 minutes. Then the solution was filtered and lignin content in the filtrate was found to be 1.6 g. The delignified biomass (residue) was treated with 5.5% of NaOH solution (about 30 mL) for about 15 minutes at 75° C. and filtered. The pH of the filtrate was adjusted to 5.2 and then, about 75 mL of ethanol was added in the solution to precipitate the hemicellulose. The hemicellulose was isolated from the solution by filtration and washed in distilled water. The weight of the hemicellulose was 2.6 g. Again the residue was treated with pre-cooled (5° C.) 7.5% NaOH solution (about 10 mL), pre-cooled (5° C.) 7% urea solution (about 10 mL) and pre-cooled (5° C.) 5% thiourea solution, for about 15 minutes. Then, the solution was filtered and residue was washed with distilled water to get the cellulose 3.8 g.

The homogeneous solution of choline chloride (ChCl, about 13.3 g), citric acid (CA, about 3.3 g) and citric acid monohydrate (CAMH, about 3.3 g) was formed at 95° C. In this solution (ChCl-CA-CAMH), 1 g of cellulose isolated from lemongrass spent biomass was added and the reaction mixture was stirred at 130° C. for 5 h to obtain a reddish or brownish colored solution. Thereafter, 200 mg of Indion 225 H was added and the whole reaction mixture stirred for 30 minutes at 130° C. Thereafter, the reaction mixture was cooled to room temperature and hybrid catalyst of γ-H-zeolite-phosphomolybdic acid (50 mg) added to it and stirring continued for another 90 minutes at 130° C. Then, the reaction mixture was extracted with ethyl acetate (about 20 mL) below the boiling point of ethyl acetate. Again the residual reaction mixtures were treated with Indion 225 H (about 100 mg) and γ-H-zeolite-phosphomolybdic acid (12 mg) and stirring continued at 130° C. for 2 h. Then, the reaction mixture was extracted with ethyl acetate (about 20 mL). Both ethyl acetate extracts were combined and concentrated in rotary evaporator under vacuum to obtain the HMF (about 300 mg, 40%). The HMF was further purified by column chromatography using silica gel (100 to 200 mesh). The column was eluted with 45% acetonitrile in dichloromethane to obtain the approximate purified HMF (about 250 mg, 35%).

Example 4

Air dried and pulverized spent mentha biomass (100 g) was extracted with mixture of hexane (about 150 mL), ethyl acetate (about 150 mL) and ethanol (about 150 mL) in a stirred reactor at 75° C. for about 5 h. The mixture of solvents was concentrated under vacuum and weight of the extract is 7.8 g (7.8%). The extract contains chlorophyll, lipids and hydrocarbons along with trace amounts of other components. After drying, the weight of the biomass was 85 g (approx). The extracted biomass (10 g) was treated with 1% $NaClO_2$ solution and kept at 65° C. for 30 minutes. Then filtered the solution and concentrated, the lignin content was 1.4 g. The delignified biomass (residue) was treated with 6% of NaOH solution (about 30 mL) for about 15 minutes at 75° C. and filtered. The pH of the filtrate was adjusted to 5.4 and then, about 65 mL of ethanol was added into the solution to precipitate the hemicellulose. The hemicellulose was isolated from the solution by filtration and washed in distilled water. The weight of the hemicellulose was 2.7 g. Again the residue was treated with pre-cooled (5° C.) 7% NaOH solution (about 10 mL) and pre-cooled (5° C.) 7% urea solution (about 10 mL) and pre-cooled (5° C.) 5% thiourea solution, for about 15 minutes. Then, the solution was filtered and the residue was washed with distilled water to get the cellulose 3.8 g.

The homogeneous solution of choline chloride (ChCl, about 13.3 g), citric acid (CA, about 3.3 g) and citric acid monohydrate (CAMH, about 3.3 g) was formed at 90° C. In this solution (ChCl-CA-CAMH), 1 g of cellulose isolated from mentha spent biomass was added and the reaction mixture stirred at 140° C. for 4 h to obtain a reddish or brownish colored solution. Thereafter, about 200 mg of Indion 225H was added followed by addition of about 0.5 mL of distilled water and the whole reaction mixture was stirred for about 20 minutes at 120° C. Thereafter the reaction mixture was cooled and hybrid catalyst of β-H-zeolite-phosphomolybdic acid (about 50 mg) added to it and stirring continued for another 2 h at 120° C. Then, the reaction mixture was extracted with ethyl acetate (about 20 mL) below the boiling point of ethyl acetate. Again, the residual reaction mixtures were treated with Indion 225H (about 100 mg) and β-H-zeolite-phosphomolybdic acid (about 15 mg) and stirring continued at 120° C. for 2 h. Then, the reaction mixture was extracted with ethyl acetate (about 20 mL). Both ethyl acetate extracts were combined and concentrated in rotary evaporator under vacuum to obtain the HMF (about 300 mg, 40%). The HMF was further purified by column chromatography using silica gel (60 to 200 mesh). The column was eluted with 45% acetonitrile in dichloromethane to obtain the approximate purified HMF (about 250 mg, 35%).

Example 5

Air dried and pulverized spent mentha biomass (100 g) was extracted with mixture of hexane (about 150 mL), ethyl acetate (about 150 mL) and methanol (about 150 mL) in a stirred reactor at 65° C. for about 5 h. The mixture of solvents was concentrated under vacuum and weight of the extract was 7.1 g (7.1%). The extract contains chlorophyll, lipids and hydrocarbons along with trace amounts of other components. After drying, the weight of the biomass was 87 g (approx). The extracted biomass (10 g) was treated with 1.1% $NaClO_2$ solution and kept at 70° C. for 30 minutes. Then the solution was filtered and concentrated, the lignin content was 1.4 g. The delignified biomass (residue) was treated with 6.5% of NaOH solution (about 30 mL) for about 15 minutes at 70° C. and filtered. The pH of the filtrate was maintained at 5.4 and then, about 70 mL of ethanol was added in the solution to precipitate the hemicellulose. The hemicellulose was isolated from the solution by filtration and washed in distilled water. The weight of the hemicellulose was 2.7 g. Again the residue was treated with pre-cooled (5° C.) 8% NaOH solution (about 10 mL) and pre-cooled (5° C.) 8% urea solution (about 10 mL) and pre-cooled (5° C.) 6.5% thiourea solution, for about 15 minutes. Then, the solution was filtered and residue was washed with distilled water and acetone to get the cellulose 3.6 g.

The homogeneous solution of choline chloride (ChCl, about 13.3 g), citric acid (CA, about 3.3 g) and citric acid monohydrate (CAMH, about 3.3 g) was formed at 85° C. In this solution (ChCl-CA-CAMH), 1 g of cellulose isolated from mentha spent biomass was added and the reaction mixture stirred at 135° C. for 4 h to obtain a reddish or brownish colored solution. Thereafter, Indion 790 (200 mg) is added and stirred the whole reaction mixture for 25 minutes at 125° C. Thereafter, the reaction mixture was cooled and hybrid catalyst β-H-zeolite-phosphomolybdic acid (50 mg) was added to it and stirring continued for another 2 h at 125° C. Then, the reaction mixture was extracted with ethyl acetate (about 20 mL) below the boiling point of ethyl acetate. Again the residual reaction mixture was treated with Indion 790 (110 mg) β-H-zeolite-phosphomolybdic acid (14 mg) and stirring continued at 125° C. for 2 h. Then, the reaction mixture was extracted with ethyl acetate (about 20 mL). Both the ethyl acetate extracts were combined and concentrated in rotary evaporator under vacuum to obtain the HMF (about 300 mg, 40%). The HMF was further purified by column chromatography using silica gel (100 to 200 mesh). The column was eluted with 40% acetonitrile in dichloromethane to obtain the approximate purified HMF (about 250 mg, 35%).

Example 6

Air dried and pulverized spent patchouli biomass (100 g) was extracted with mixture of hexane (about 150 mL), ethyl acetate (about 150 mL) and ethanol (about 150 mL) in a stirred reactor at 70° C. for about 5 h. The mixture of solvents was concentrated under vacuum and weight of the extract was 7.2 g (7.2%). The extract contains chlorophyll, lipids and hydrocarbons along with trace amounts of other components. After drying, the weight of the biomass was 88 g (approx). The extracted biomass (10 g) was treated with 1% $NaClO_2$ solution and kept at 80° C. for 30 minutes. Then the solution was filtered and concentrated and the lignin content in the filtrate was found to be 1.7 g. The delignified biomass (residue) was treated with 6% of NaOH solution (about 30 mL) for about 15 minutes at 70° C. and filtered. The pH of the filtrate was adjusted to 5.3 and then, about 80 mL of ethanol was added in the solution to precipitate the hemicellulose. The hemicellulose was isolated from the solution by filtration and washed in distilled water. The weight of the hemicellulose was 2.7 g. Again the residue was treated with pre-cooled (5° C.) 7% NaOH solution (about 10 mL) and pre-cooled (5° C.) 7% urea solution (about 10 mL) and pre-cooled (5° C.) 5.5% thiourea solution, for about 15 minutes. Then, the solution was filtered and the residue was washed with distilled water to get the cellulose 3.5 g.

The homogeneous solution of choline chloride (ChCl, about 13.3 g), citric acid (CA, about 3.3 g) and citric acid monohydrate (CAMH, about 3.3 g) was formed at 95° C. In this solution (ChCl-CA-CAMH), 1 g of cellulose isolated from patchouli spent biomass was added and stirred the reaction mixture at 135° C. for 4 h to obtain a reddish or brownish coloured solution. Thereafter, Indion 790 (210 mg) was added and the whole reaction mixture was stirred for 10 minutes at 125° C. Then, the reaction mixture was cooled to room temperature and 0.5 mL of distilled water added to it, followed by stirring at 125° C. for 20 minutes. Thereafter, the reaction mixture was cooled (80° C.) and to it, hybrid catalyst γ-H-zeolite-phosphomolybdic acid (50 mg) was added and stirring continued for another 90 minutes at 125° C. Then, the reaction mixture was extracted with ethyl acetate (about 20 mL) below the boiling point of ethyl acetate. Again the residual reaction mixtures were treated with Indion 790 (100 mg) β-H-zeolite-phosphomolybdic acid (13 mg) and stirring continued at 125° C. for 2 h. Then, the reaction mixture was extracted with ethyl acetate (about 20 mL). Both the ethyl acetate extracts were combined and concentrated in rotary evaporator under vacuum to obtain the HMF (about 300 mg, 40%). The HMF is further purified by column chromatography using silica gel (60 to 120 mesh). The column was eluted with 35% acetonitrile in dichloromethane to obtain the approximate purified HMF (about 250 mg, 35%).

Example 7

The pure cellulose (10 g cotton) was treated with pre-cooled (5° C.) 7% NaOH solution (about 15 mL) and pre-cooled (5° C.) 12% urea solution (about 15 mL), for about 15 minutes. Then the solution was filtered and the residue was washed with distilled water to get processed cellulose (about 9 g). The homogeneous solution of choline chloride (ChCl, about 13.3 g), citric acid (CA, about 3.3 g) and citric acid monohydrate (CAMH, about 3.3 g) was formed at 85° C. In this solution (ChCl-CA-CAMH), 1 g of the above processed cellulose was added and the reaction mixture stirred at 140° C. for 4 h to obtain a reddish or brownish coloured solution. Thereafter, 220 mg of Indion 225H was added followed by addition of about 0.5 mL of distilled water and the whole reaction mixture was stirred for about 20 minutes at 125° C. Thereafter, the reaction mixture was cooled and hybrid catalyst of γ-H-zeolite-phosphomolybdic acid (about 50 mg) was added and stirring continued for another 2 h at 125° C. Then, the reaction mixture was extracted with ethyl acetate (about 20 mL) below the boiling point of ethyl acetate. Again, the residual reaction mixtures were treated with Indion 225H (100 mg) and γ-H-zeolite-phosphomolybdic acid (about 14 mg) and stirring continued at 125° C. for 2 h. Then, the reaction mixture was extracted with ethyl acetate (about 20 mL). Both ethyl acetate extracts were combined and concentrated in rotary evaporator under vacuum to obtain the HMF (about 310 mg, 44%). The HMF was further purified by column chromatography using silica gel (100 to 200 mesh). The column was eluted with 40% acetonitrile in dichloromethane to obtain the approximate purified HMF (about 260 mg, 37%).

Example 8

The homogeneous solution of choline chloride (ChCl, about 13.3 g) citric acid (CA, about 3.3 g) and citric acid monohydrate (CAMH, about 3.3 g) was formed at 90° C. In this solution (ChCl-CA-CAMH), 1 g of microcrystalline cellulose was added and the reaction mixture was stirred at 140° C. for 4 h to obtain a reddish or brownish coloured solution. Thereafter, 210 mg of Indion 790 was added followed by addition of about 0.5 mL of distilled water and the whole reaction mixture was stirred for 20 minutes at 130° C. Thereafter, the reaction mixture was cooled and hybrid catalyst of γ-H-zeolite-phosphomolybdic acid (about 50 mg) added and stirring continued for another 2 h at 130° C. Then, the reaction mixture was extracted with ethyl acetate (about 20 mL) below the boiling point of ethyl acetate. Again, the residual reaction mixtures were treated with Indion 790 (100 mg) and γ-H-zeolite-phosphomolybdic acid (about 15 mg) and stirring continued at 130° C. for 2 h. Then, the reaction mixture was extracted with ethyl acetate (about 20 mL). Both ethyl acetate extracts were combined and concentrated in rotary evaporator under vacuum to obtain the HMF (about 252 mg, 36%). The HMF was further purified by column chromatography using silica gel (60 to 200 mesh). The column was eluted with 35% acetonitrile in dichloromethane to obtain the approximate purified HMF (about 210 mg, 30%).

Example 9

The pure microcrystalline cellulose (10 g, supplied by Sigma-Aldrich) was treated with pre-cooled (5° C.) 7% NaOH solution (about 10 mL), pre-cooled (5° C.) 7% urea solution (about 10 mL) and pre-cooled (5° C.) thiourea solution 5.5% (about 10 mL), for about 15 minutes. Then the solution was filtered and the residue was washed with distilled water to get processed microcrystalline cellulose (about 9.4 g). The homogeneous solution of choline chloride (ChCl, about 13.3 g), citric acid (CA, about 3.3 g) and citric acid monohydrate (CAMH, about 3.3 g) was formed at 85° C. In this solution (ChCl-CA-CAMH), 1 g of above microcrystalline processed cellulose was added and the reaction mixture stirred at 135° C. for 4 h to obtain a reddish or brownish coloured solution. Thereafter, 200 mg of Indion 790 was added followed by addition of about 0.5 mL of distilled water and the whole reaction mixture stirred for 20 minutes at 130° C. Thereafter, the reaction mixture was cooled and the hybrid catalyst of β-H-zeolite-phosphomolybdic acid (about 55 mg) was added and stirring continued for another 2 h at 130° C. Then, the reaction mixture was extracted with ethyl acetate (about 20 mL) below the boiling point of ethyl acetate. Again, the residual reaction mixture was treated with Indion 790 (110 mg) and β-H-zeolite-phosphomolybdic acid (about 15 mg) and stirring continued at 130° C. for 2 h. Then, the reaction mixture was extracted with ethyl acetate (about 20 mL). Both the ethyl acetate extracts were combined and concentrated in rotary evaporator under vacuum to obtain the HMF (about 320 mg, 45%). The HMF was further purified by column chromatography using silica gel (60 to 120 mesh). The column was eluted with 45% acetonitrile in dichloromethane to obtain the approximate purified HMF (about 270 mg, 38%).

Example 10

The reacted solvent system obtained from Example 9 was diluted with 50 ml methanol and filtered. The filtrate was treated with 3 g charcoal and again filtered. The filtrate was concentrated to recover the solvent system comprising the mixture of choline chloride, citric acid and citric acid monohydrate (14 g). In this solvent system (ChCl-CA-CAMH), again choline chloride (ChCl, about 4 g) citric acid (CA, about 1 g) and citric acid monohydrate (CAMH, about 1 g) was added and made homogeneous solution at 85° C. In this final solvent system (ChCl-CA-CAMH), 1 g of above microcrystalline processed cellulose (Example 9) was added and the reaction mixture stirred at 135° C. for 4 h to obtain a reddish or brownish coloured solution. Thereafter, 200 mg of Indion 225H was added followed by addition of about 0.5 mL of distilled water and stirred the whole reaction mixture for 20 minutes at 130° C. Thereafter, the reaction mixture was cooled and hybrid catalyst of β-H-zeolite-phosphomolybdic acid (about 55 mg) added and stirring continued for another 2 h at 130° C. Then, the reaction mixture was extracted with ethyl acetate (about 20 mL) below the boiling point of ethyl acetate. Again, the residual reaction mixture was treated with Indion 225H (110 mg) and β-H-zeolite-phosphomolybdic acid (about 15 mg) and stirring continued at 130° C. for 2 h. Then, the reaction mixture was extracted with ethyl acetate (about 20 mL). Both ethyl acetate extracts were combined and concentrated in rotary evaporator under vacuum to obtain the HMF (about 320 mg, 45%). The HMF was further purified by column chromatography using silica gel (60 to 200 mesh). The column was eluted with 40% acetonitrile in dichloromethane to obtain the approximate purified HMF (about 270 mg, 38%).

Example 11

After reaction, final spent reaction mixture was treated with 50 ml ethanol. Then, diluted reaction mixture was filtered, washed in hot water. The catalysts viz. Indion 225H (about 300 mg) and β-H-zeolite-phosphomolybdic acid (about 50 mg) were isolated. The Indion 225H was washed in ethanol again and oven dried at 60° C. Similarly, β-H-zeolite-phosphomolybdic acid was calcinated at 500° C. for 8 h. The homogeneous solution of choline chloride (ChCl, about 6.7 g) citric acid (CA, about 1.7 g) and citric acid monohydrate (CAMH, about 1.7 g) was formed at 85° C. In this solution (ChCl-CA-CAMH), 500 mg of above microcrystalline processed cellulose (Example 9) was added and the reaction mixture was stirred at 135° C. for 4 h to obtain a reddish or brownish coloured solution. Thereafter, 100 mg of Indion 225H (mentioned above) was added followed by addition of about 0.5 mL of distilled water and the whole reaction mixture was stirred for 20 minutes at 130° C. Thereafter, the reaction mixture was cooled and hybrid catalyst of β-H-zeolite-phosphomolybdic acid (about 28 mg) was added and stirring continued for another 2 h at 130° C. Then, the reaction mixture was extracted with ethyl acetate (about 15 mL) below the boiling point of ethyl acetate. Again, the residual reaction mixture was treated with Indion 225H (55 mg) and β-H-zeolite-phosphomolybdic acid (about 8 mg) and stirring continued at 130° C. for 2 h. Then, the reaction mixture was extracted with ethyl acetate (about 15 mL). Both ethyl acetate extracts were combined and concentrated in rotary evaporator under vacuum to obtain the HMF (about 162 mg, 45%). The HMF was further purified by column chromatography using silica gel (100 to 200 mesh). The column was eluted with 35% acetonitrile in dichloromethane to obtain the approximate purified HMF (about 136 mg, 38%).

Example 12

The pure microcrystalline cellulose (10 g, supplied by Sigma-Aldrich) was treated with pre-cooled (5° C.) 7% NaOH solution (about 10 mL), pre-cooled (5° C.) 7% urea solution (about 10 mL) and pre-cooled (5° C.) thiourea solution 5.5% (about 10 mL), for about 15 minutes. Then filter the solution and residue was washed with distilled water to get processed microcrystalline cellulose (about 9.5 g). The homogeneous solution of choline chloride (ChCl, about 13.3 g), citric acid (CA, about 3.3 g) and citric acid monohydrate (CAMH, about 3.3 g) was formed at 85° C. In this solution, (ChCl-CA-CAMH), 1 g of above processed microcrystalline cellulose was added and the reaction mixture stirred at 135° C. for 3 h to obtain a reddish or brownish coloured solution. Thereafter, 250 mg of Indion 225H was added followed by hybrid catalyst β-H-zeolite-phosphomolybdic acid (about 60 mg) and stirring continued at 125° C. The reaction mixture was supplied methyl isobutyl ketone (MIBK) in continuous mode at one side, and HMF solution (with MIBK) was collected on another side with solvent retention time of 10 minutes. Finally, after about 2 h of MIBK solution collection, the combined extract was concentrated in rotary evaporator under vacuum to obtain the HMF (about 315 mg, 45%). The HMF was further purified by column chromatography using silica gel (60 to 120 mesh). The column was eluted with 40% acetonitrile in dichloromethane to obtain the approximate purified HMF (265 mg, 37%).

Advantages of the Present Invention

I. The process described in this invention uses a newer combination of choline chloride-citric acid-citric acid monohydrate for the dissolution of cellulose. The solvent system is economical and re-usable in number of batches. Thus it can be adapted to commercial production of hydroxymethyl furfural (HMF).
II. The catalysts, un-reacted cellulose and solvents used in the reaction can be recycled. Thus, this process is cost effective.
III. This process is operated at workable temperature and atmospheric pressure, thus, the process is suitable for large scale production and is cost effective.
IV. The solvents used in the reaction are common organic solvents and these solvents are easily removed by distillation process. Thus the process is cost effective.
V. The process can be operated in batch as well as in continuous mode.
VI. The cellulose used in the reaction is isolated from waste aromatic biomass. These aromatic biomasses are available abundantly throughout the Globe. The process would be economical and solve the environmental related issues. Thus the process is very attractive for production of biochemicals and biofuel.
VII. The new combination of catalyst system i.e. Indion 225H or Indion 790 and hybrid catalyst γ-H-zeolite-phosphomolybdic acid or β-H-zeolite-phosphomolybdic acid. In this combination, the first category of catalysts is acidic type, which helps in depolymerization of cellulose followed by the second category of catalysts which helps in the synthesis of HMF. The advantages of these catalysts are:
Indion catalysts are economical in comparison to metal chloride catalysts or Dowex resin.
Conversion efficiency and purity of HMF obtained in ChCl-CA-CAMH system using Indion catalyst is better in comparison to metal chlorides or Dowex resins.
The combined catalytic system i.e. zeolite-phosphomolybdic acid is more effective and selective for synthesis of HMF in comparison to individual zeolite and phosphomolybdic acid catalyst. The zeolite-phosphomolybdic acid is thermally stable more than 550° C.
Two phase catalyst treatment increased the yield and purity of HMF in ChCl-CA-CAMH eutectic solvent system in comparison to other metal chlorides and resins reported in ionic liquid solvent system.

We claim:
1. A green process for the production of 5-Hydroxymethyl furfural (HMF) comprising the following steps:
  (a) dissolving cellulose in a choline chloride-citric acid-citric acid monohydrate system to obtain a solution;
  (b) adding a solid acidic catalyst to the solution as obtained in step (a) and reacting for a period ranging between 5 to 25 minutes followed by adding a hybrid catalyst and then reacting for a period ranging between 90 to 120 minutes to allow the formation of a reaction mixture;
  (c) extracting the reaction mixture as obtained in step (b) with a liquid solvent selected from the group consisting of ethyl acetate and methyl isobutyl ketone to obtain a first liquid solvent extract containing 5-Hydroxymethyl furfural and a residual reaction mixture;
  (d) treating the residual reaction mixture as obtained in step (c) with the solid acidic catalyst followed by treating with the hybrid catalyst and extracting as provided in step (b) and (c) to obtain a second liquid solvent extract containing 5-Hydroxymethyl furfural and a residual reaction mixture;
  (e) combining the liquid solvent extracts obtained in step (c) and step (d) and distilling the combined extract to extract 5-Hydroxymethyl furfural, followed by purification of 5-Hydroxymethyl furfural by column chromatography,
  wherein the hybrid catalyst used in steps (b) and (d) is selected from the group consisting of γ-H-zeolite-phosphomolybdic acid and β-H-zeolite-phosphomolybdic acid, and
  wherein the solid acidic catalyst used in steps (b) and (d) is selected from the group consisting of Indion 225H and Indion 790.
2. The process as claimed in claim 1, wherein steps (a) and (b) are carried out at a temperature in the range of 120° C. to 140° C.
3. The process as claimed in claim 1, wherein the cellulose used in step (a) is prepared by a process comprising the following steps:
  (i) pulverizing dried spent biomass obtained from an aromatic crop selected from the group consisting of mentha, palmarosa, lemongrass and patchouli to size less than 0.1 mm;

(ii) treating pulverized spent biomass with a mixture of equal amounts of solvent (hexane:ethyl acetate:alcohol) to isolate lipids and waxes for obtaining defatted biomass;

(iii) treating the defatted biomass as obtained in step (ii) with aqueous $NaClO_2$ solution followed by aqueous NaOH solution, to obtain a residue;

(iv) treating the residue obtained in step (iii) with combination of pre-cooled aqueous NaOH, urea and thiourea solution to obtain processed cellulose.

4. The process as claimed in claim 1, wherein the choline chloride-citric acid-citric acid monohydrate system used in step (a) is prepared by mixing choline chloride, citric acid and citric acid monohydrate in the ratio of 4:1:1 (by weight) at 85 to 95° C.

5. The process as claimed in claim 1, wherein the hybrid catalyst selected from the group consisting of γ-H-zeolite-phosphomolybdic acid and β-H-zeolite-phosphomolybdic acid is synthesized by a process comprising the following steps:

[i] mixing 55-65% of phosphomolybdic acid (heteropoly acid) and 35-45% of zeolite selected from the group consisting of γ-H-zeolite and β-H-zeolite, in aqueous medium followed by stirring the mixture for a period ranging between 1 to 2 h to obtain a reaction mixture;

[ii] drying the reaction mixture as obtained in step (i) followed by calcinating at a temperature ranging between 500° C. to 550° C. to obtain the hybrid catalyst.

6. The process as claimed in claim 5, wherein calcination in step (ii) is performed for a period of 7 to 8 h.

7. The process as claimed in claim 1, wherein the solid acidic catalyst, the hybrid catalyst and the choline chloride-citric acid-citric acid monohydrate system from the reaction mixture obtained in step (d) are recycled for reuse.

8. The process as claimed in claim 7, wherein the solid acidic catalyst and the hybrid catalyst are recycled by a process comprising the following steps:

i. diluting the residual reaction mixture as obtained in step (d) of claim 1 with alcoholic solvent selected from the group consisting of methanol and ethanol to obtain a precipitate of un-reacted cellulose and a mixture of catalysts;

ii. washing the precipitate with water to remove the unwanted carbon particles followed by separating the un-reacted cellulose and mixture of catalysts by gravity separation technique;

iii. separating the solid acidic catalyst and the hybrid catalyst from the mixture of catalysts by gravity separation technique, followed by washing with water and ethanol and drying;

iv. calcinating the hybrid catalyst at a temperature ranging between 500 to 550° C.

9. The process as claimed in claim 7, wherein the choline chloride-citric acid-citric acid monohydrate system is recycled by a process comprising the following steps:

[i] diluting the residual reaction mixture as obtained in step (d) of claim 1 with an alcoholic solvent selected from the group consisting of methanol and ethanol to dissolve the choline chloride-citric acid-citric acid monohydrate;

[ii] filtering the solution to obtain a filtrate and charcoaling the filtrate for removing dark red colored material from the filtrate;

[iii] concentrating the charcoaled filtrate under vacuum to obtain the choline chloride-citric acid-citric acid monohydrate system.

10. The process as claimed in claim 1, wherein concentration of the liquid solvent extract in step (e) is done by distillation to obtain the 5-Hydroxymethyl furfural.

11. The process as claimed in claim 1, wherein the 5-Hydroxymethyl furfural is purified by column chromatography using 60 to 200 mesh size silica gel and 35 to 45% acetonitrile in dichloromethane.

* * * * *